(12) United States Patent
Castaneda et al.

(10) Patent No.: US 8,518,088 B2
(45) Date of Patent: Aug. 27, 2013

(54) METHOD OF BENDING BONE PLATE WITH BENDING TOOLS

(75) Inventors: Alfredo Castaneda, Miami, FL (US); Joel G. Marquart, Pembroke Pines, FL (US); Eduardo A. Ampuero, Miami, FL (US); Keith R. Alexander, West Palm Beach, FL (US)

(73) Assignee: Biomet C.V., Gibraltar (GI)

( * ) Notice: Subject to any disclaimer, the term of this patent is extended or adjusted under 35 U.S.C. 154(b) by 0 days.

(21) Appl. No.: 13/600,959

(22) Filed: Aug. 31, 2012

(65) Prior Publication Data

US 2013/0006311 A1   Jan. 3, 2013

Related U.S. Application Data

(60) Division of application No. 12/276,569, filed on Nov. 24, 2008, now Pat. No. 8,292,898, which is a continuation of application No. 12/210,617, filed on Sep. 15, 2008.

(51) Int. Cl.
*A61B 17/88* (2006.01)

(52) U.S. Cl.
USPC .......................................... 606/281; 606/101

(58) Field of Classification Search
USPC .............................. 606/86 A, 86 B, 86 R, 96
See application file for complete search history.

(56) References Cited

U.S. PATENT DOCUMENTS

| | | |
|---|---|---|
| 4,573,458 A | 3/1986 | Lower |
| 4,903,691 A | 2/1990 | Heinl |
| 4,905,679 A | 3/1990 | Morgan |
| 4,959,065 A | 9/1990 | Arnett et al. |
| 4,966,599 A | 10/1990 | Pollock |
| 5,087,259 A | 2/1992 | Krenkel |
| 5,336,224 A | 8/1994 | Selman |
| 5,372,598 A | 12/1994 | Luhr et al. |
| 5,607,427 A | 3/1997 | Tschakaloff |
| 5,681,313 A | 10/1997 | Diez |
| 5,690,631 A | 11/1997 | Duncan et al. |
| 5,718,705 A | 2/1998 | Sammarco |
| 5,766,221 A | 6/1998 | Benderev et al. |
| 5,779,706 A | 7/1998 | Tschakaloff |
| 5,785,712 A | 7/1998 | Runciman et al. |

(Continued)

FOREIGN PATENT DOCUMENTS

| | | |
|---|---|---|
| DE | 102005032026 B3 | 12/2006 |
| WO | WO99/38448 | 8/1999 |
| WO | WO2005/060846 | 7/2005 |
| WO | WO2007/006430 | 1/2007 |

OTHER PUBLICATIONS

Hand Surgery Integrated Solutions Brochure, STRYKER, Literature No. 90-077 00, Print Date Oct. 2006 Rev. 1.
LCP Compact Foot/Compact Hand Technique Guide, SYNTHES 2006.

(Continued)

*Primary Examiner* — Nicholas Woodall
*Assistant Examiner* — Larry E Waggle, Jr.
(74) *Attorney, Agent, or Firm* — Gordon & Jacobson, PC

(57) ABSTRACT

Plate shaping tools may be attached to a plate having pre-assembled guides while the plate is located on the bone to effect alteration of the plate shape in an effective and precise manner. The tools are designed such that a drill and K-wires can be inserted through the guides while the tools are coupled to the guides. In accord with tools disclosed and methods described, the plates are reconfigurable in shape.

17 Claims, 16 Drawing Sheets

(56) References Cited

U.S. PATENT DOCUMENTS

| | | | |
|---|---|---|---|
| 5,980,540 | A | 11/1999 | Bruce |
| 5,984,925 | A | 11/1999 | Apgar |
| 6,093,188 | A | 7/2000 | Murray |
| 6,355,042 | B2 | 3/2002 | Winquist et al. |
| 6,524,318 | B1 | 2/2003 | Longhini et al. |
| 6,652,530 | B2 | 11/2003 | Ip et al. |
| 6,692,497 | B1 | 2/2004 | Tormala et al. |
| 6,786,909 | B1 | 9/2004 | Dransfeld et al. |
| 6,866,665 | B2 | 3/2005 | Orbay |
| 7,052,499 | B2 | 5/2006 | Steger et al. |
| 7,635,381 | B2 | 12/2009 | Orbay |
| 7,740,634 | B2 * | 6/2010 | Orbay et al. .................. 606/101 |
| 8,348,980 | B2 * | 1/2013 | Prasad et al. .................. 606/282 |
| 2002/0004660 | A1 | 1/2002 | Henniges |
| 2003/0055429 | A1 | 3/2003 | Ip et al. |
| 2003/0083667 | A1 | 5/2003 | Ralph et al. |
| 2004/0034356 | A1 | 2/2004 | LeHuec et al. |
| 2004/0049193 | A1 | 3/2004 | Capanni |
| 2004/0186482 | A1 | 9/2004 | Kolb et al. |
| 2004/0204717 | A1 | 10/2004 | Fanger et al. |
| 2004/0210220 | A1 | 10/2004 | Tornier |
| 2005/0273104 | A1 | 12/2005 | Oepen et al. |
| 2005/0288790 | A1 | 12/2005 | Swords |
| 2006/0149250 | A1 | 7/2006 | Castaneda et al. |
| 2006/0149265 | A1 | 7/2006 | James et al. |
| 2006/0161158 | A1 | 7/2006 | Orbay et al. |
| 2006/0173459 | A1 | 8/2006 | Kay et al. |
| 2006/0217722 | A1 | 9/2006 | Dutoit et al. |
| 2006/0241607 | A1 | 10/2006 | Myerson et al. |
| 2006/0241608 | A1 | 10/2006 | Myerson et al. |
| 2006/0276787 | A1 | 12/2006 | Zubok et al. |
| 2007/0233111 | A1 | 10/2007 | Orbay et al. |
| 2009/0118768 | A1 | 5/2009 | Sixto, Jr. et al. |

OTHER PUBLICATIONS

Stryker Hand Plating System, Stryker, 2007, available at http://www.chirruky.eu/medical/firmy/Stryker/variax%20hand.pdf (The last page of this document consists of an enlargement of the legal section, showing the date of 2007 more legibly).

* cited by examiner

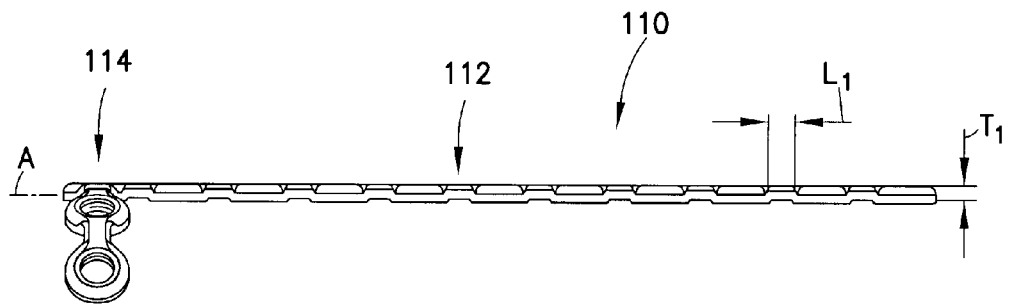
FIG.5
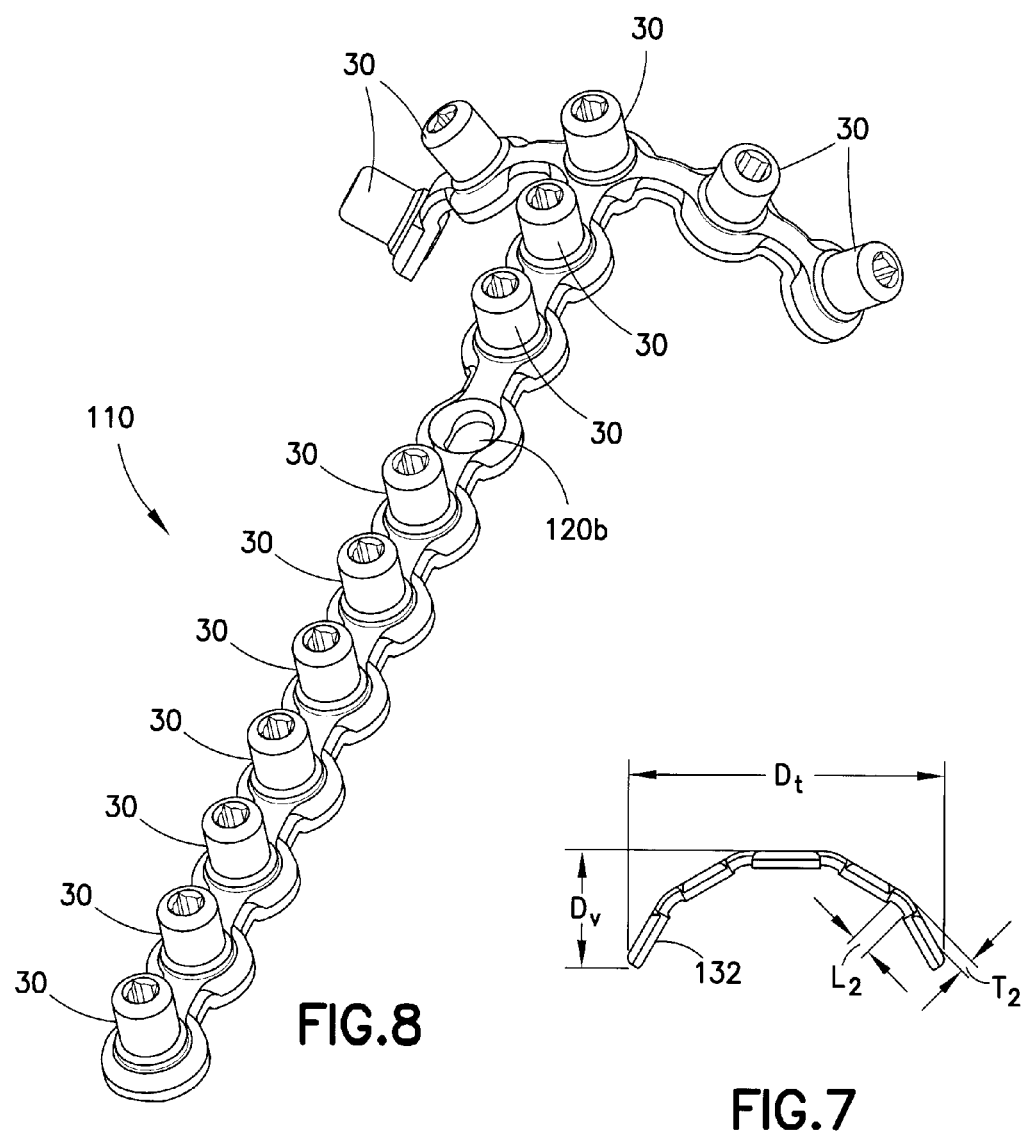
FIG.8
FIG.7

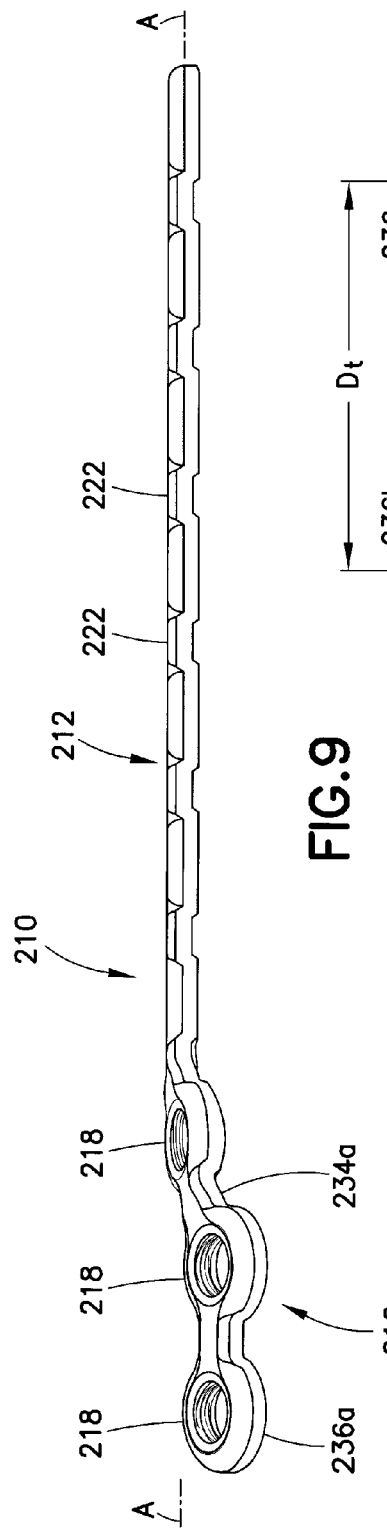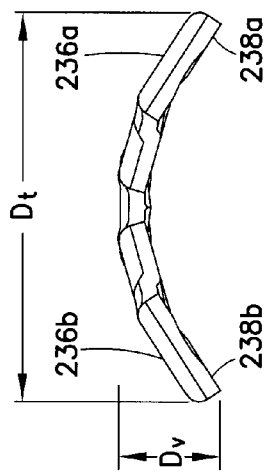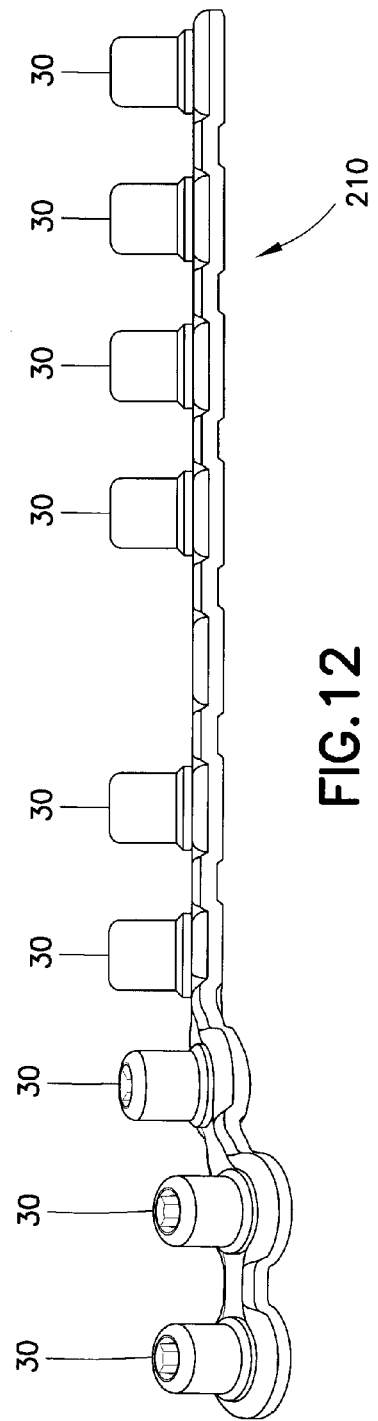

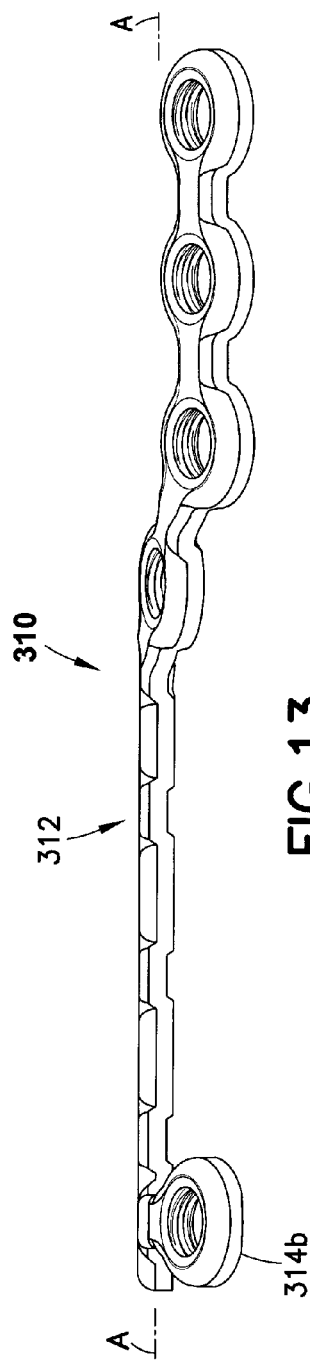
FIG.13
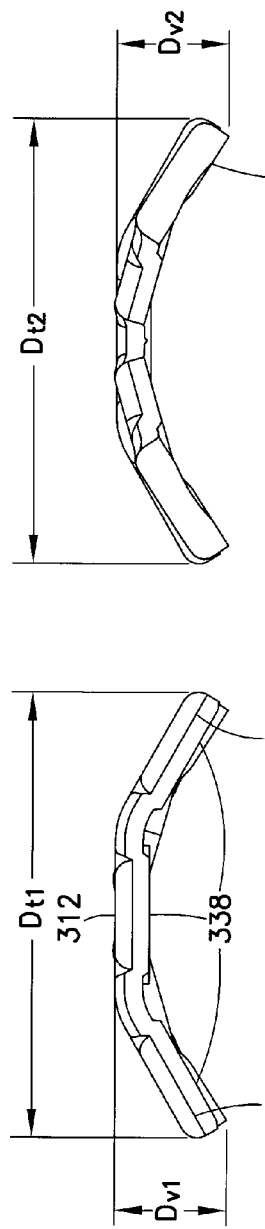
FIG.15
FIG.16
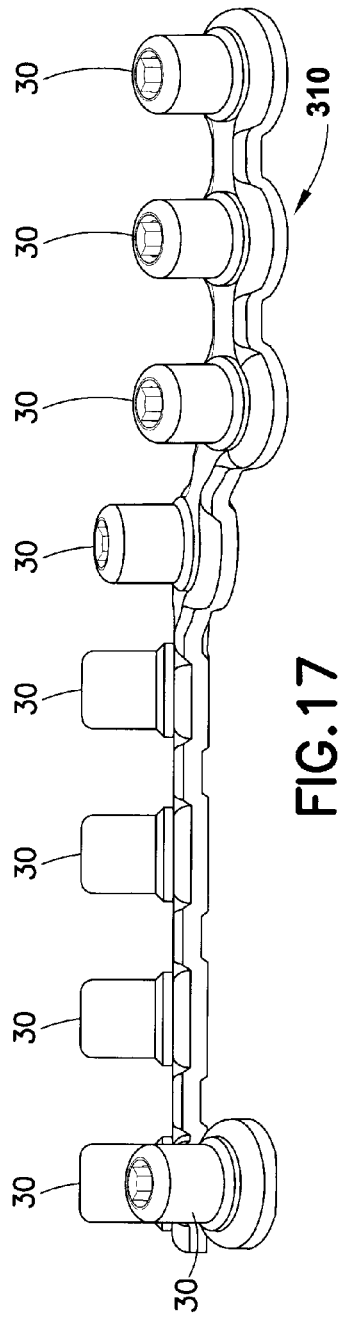
FIG.17

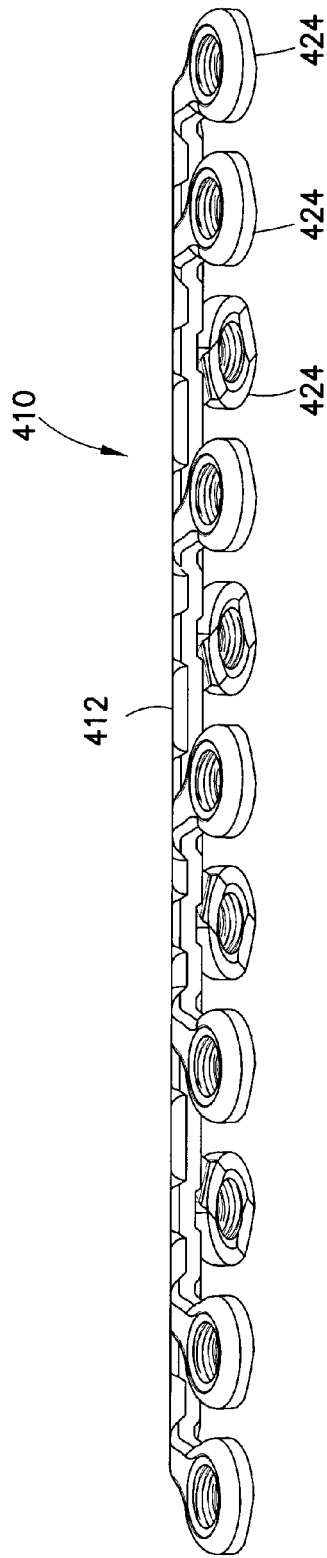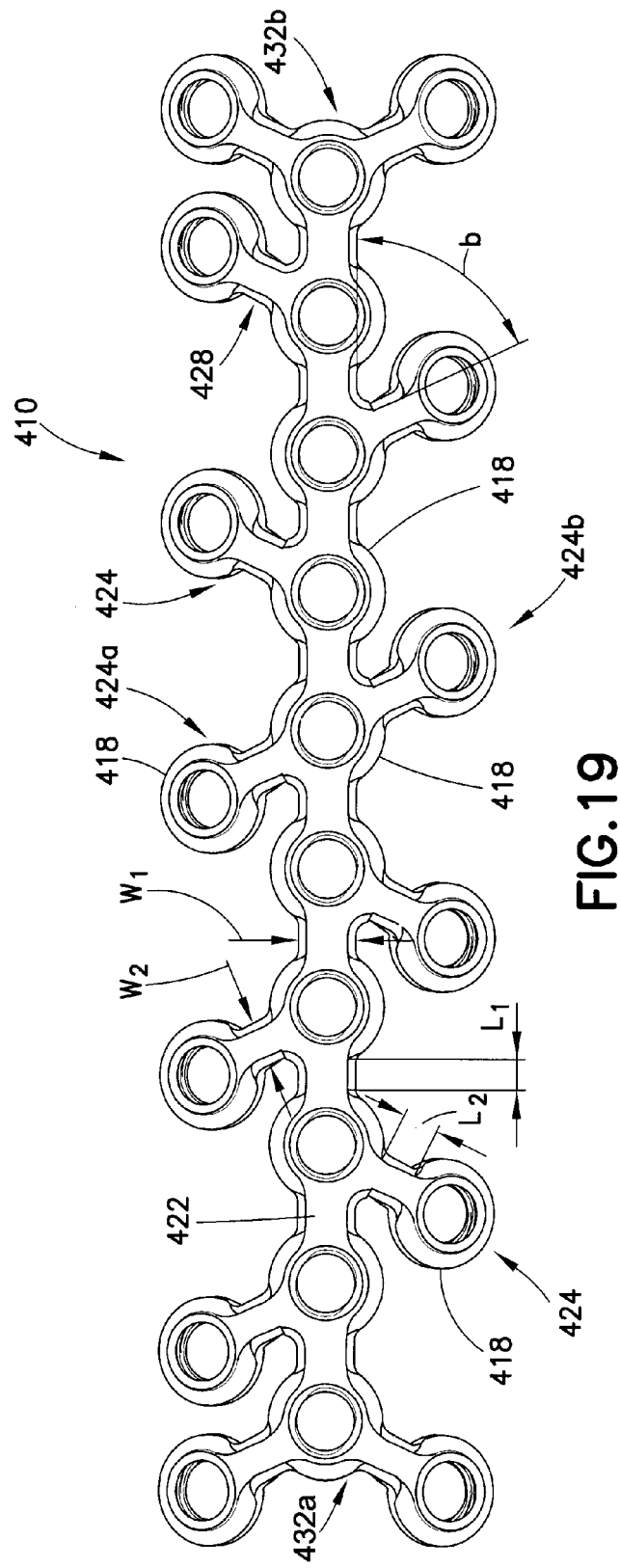

METHOD OF BENDING BONE PLATE WITH BENDING TOOLS

CROSS-REFERENCE TO RELATED APPLICATION

This application is a divisional of U.S. Ser. No. 12/276,569, filed Nov. 24, 2008, issued on Oct. 23, 2012, as U.S. Pat. No. 8,292,898, which is a continuation of U.S. Ser. No. 12/210,617, filed Sep. 15, 2008, both of which are hereby incorporated by reference in their entireties.

BACKGROUND OF THE INVENTION

1. Field of the Invention

This invention relates broadly to surgical devices and methods for the internal fixation of fractured bones. More particularly, this invention relates to tools to shaping bone plates and usable in combination with other tools and fasteners.

2. State of the Art

Metacarpal fractures are the most common fracture affecting the hand, accounting for about 48% of hand injuries and 12% of all types of fractures. Phalangeal fractures account for about 40% of hand injuries and 10% of all fractures. Displaced metacarpal and phalangeal fractures should be treated with open reduction and internal fixation with screws and very small bone plates.

Bone plate systems for hand fractures are currently available in the small sizes required for placement on metacarpal and phalangeal bones. For example, the Stryker Profyle Small Bone Plating System is specifically designed for fractures of the metacarpal and phalangeal bones. The system includes a set of small plates in several shapes includes straight, T-shaped, L-shaped, and ladder configuration with parallel rails and rungs extending across the rails connecting the locations of various fixation holes. By way of another example, the Synthes Compact Hand system includes straight, T-shaped, and Y-shaped plates for the fixation of fractures of the hand. The plates in the system can be bent in an attempt to approximate the contour of the bone. In order to bend a plate, a pair of pliers are used on opposing sides of the portion intended to be bent, or two rods are threadably coupled directly into a limited number of round threaded holes in the plate and force is applied to the rods to bend the plate. In either method, the plate is bent off the bone through trial and error. In addition, the plates may be trimmed to length and then subsequently deburred, also while off the bone to permit the cutting pliers proper access to the plate.

SUMMARY OF THE INVENTION

A bone plate system for the internal fixation of small bones, such as metacarpal and phalangeal bones of the hand, is provided. Each plate includes a straight rail with a longitudinal axis. The rail includes a linear arrangement of ring-shaped screw hole boundaries, with adjacent boundaries interconnected by a web having a width and a thickness. Each boundary defines a screw hole for receiving a screw. Each screw hole may be any one of a locking screw hole, a non-locking screw hole, and an elongated hole. In various embodiments one or more extensions extends non-axially from the rail. The extensions each include one or more screw hole boundaries, each boundary including a screw hole and linearly connected to the rail or another boundary by a web.

Preferred shapes for plates of the system, to accommodate the bones of the hand, include a straight plate, a T-shaped plate, a Y-shaped plate, a plate having a Y-shape at one end and a T-shape at its opposite end (a TY-shaped plate), and a 'web' plate having one or more extensions, each extension with one screw how boundary and extending from the location of a hole in the rail of the plate. The arms of the Y-shaped plate and TY-shaped plate form a net or cage along the shaft of a bone for high energy or segmental bone loss applications. This can be accomplished by bringing in the extensions along the bone shaft and leaving them unfilled. In addition, the extensions of the web plate are staggered such that the trajectories of the axes of the holes in the extensions do not intersect the trajectories of the axes of the holes in the rail.

The plates are reconfigurable in shape, even while the plate is located on the bone. The plates are preferably provided pre-assembled with guides at any one of, and preferably each of, the threaded holes. Plate shaping tools may be attached to the guides and/or plate while the plate is located on the bone to effect alteration of the plate shape in an effective and precise manner. In addition, the guides can be used to aid drilling holes for fasteners to couple the plate to bone. The tools are designed such that a drill and K-wires can be inserted through the guides while the tools are coupled to the guides. Further, the plate shaping tools at the guides and/or pliers directly on the plate can be used to repeatedly stress a web location and purposefully cause a clean break to alter the size and/or shape of a plate to better accommodate the anatomy.

The boundaries of the plates surrounding the screw holes are very thin, and a small locking screw with a low profile head design is provided for use therewith. The locking screw has a socket with a flat bottom recess that optimizes the material thickness between the socket and a lower surface of the head to provide sufficient driver engagement without reducing the torsional strength of the head to shank attachment relative to screws designed for larger plates.

Additional objects and advantages of the invention will become apparent to those skilled in the art upon reference to the detailed description taken in conjunction with the provided figures.

BRIEF DESCRIPTION OF THE DRAWINGS

FIG. 5 is a side elevation of a T-shaped plate according to the system of the invention.

FIG. 7 is an end view of the T-shaped plate of FIG. 5.

FIG. 8 is a view similar to FIG. 6, shown with guides pre-assembled within the locking screw holes of the plate.

FIG. 9 is a side elevation of a Y-shaped plate according to the system of the invention.

FIG. 11 is an end view of the Y-shaped plate of FIG. 9.

FIG. 12 is a view similar to FIG. 9, shown with guides pre-assembled within the locking screw holes of the plate.

FIG. 13 is a side elevation of a TY-shaped plate according to the system of the invention.

FIG. 15 is a first end view of the TY-shaped plate of FIG. 13.

FIG. 16 is a second end view of the TY-shaped plate of FIG. 13.

FIG. 17 is a view similar to FIG. 13, shown with guides pre-assembled within the locking screw holes of the plate.

FIG. 18 is a side elevation of a web plate according to the system of the invention.

FIG. 19 is a plan view of the web plate of FIG. 18.

DETAILED DESCRIPTION OF THE PREFERRED EMBODIMENTS

A bone plate system for the internal fixation of small bones, such as metacarpal and phalangeal bones of the hand, is provided and includes bone plates 10 (FIGS. 1 through 3), 110 (FIGS. 5 through 8), 210 (FIGS. 9 through 12), 310 (FIGS. 13 through 17), and 410 (FIGS. 18 through 22).

Figure 1:
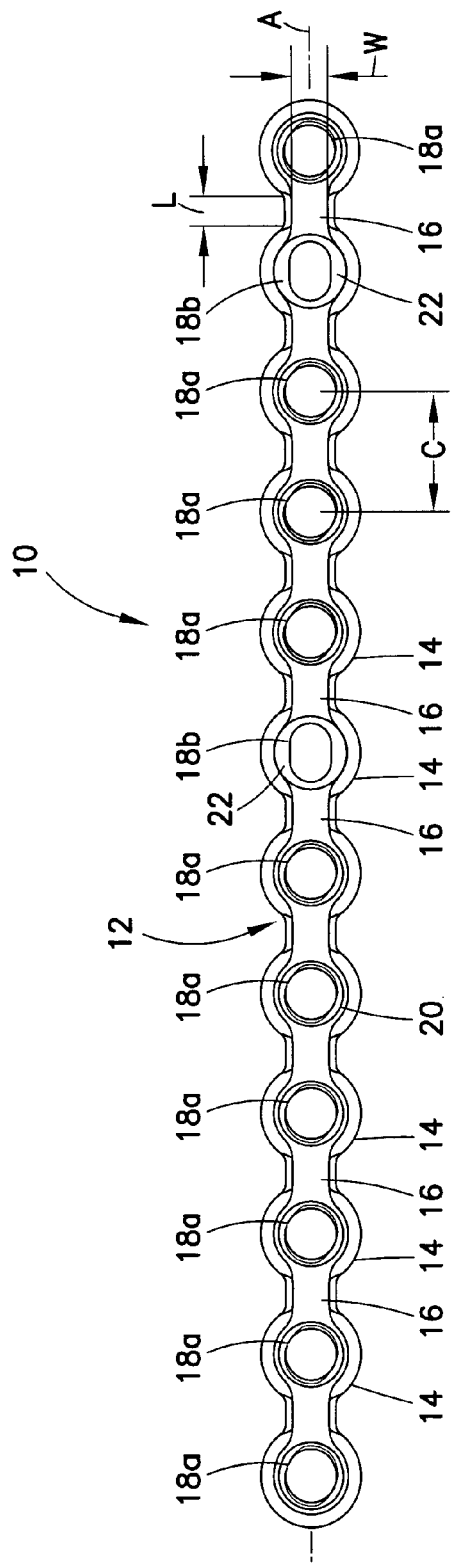
FIG. 1 is a plan view of a straight plate according to the system of the invention.
Figure 2:
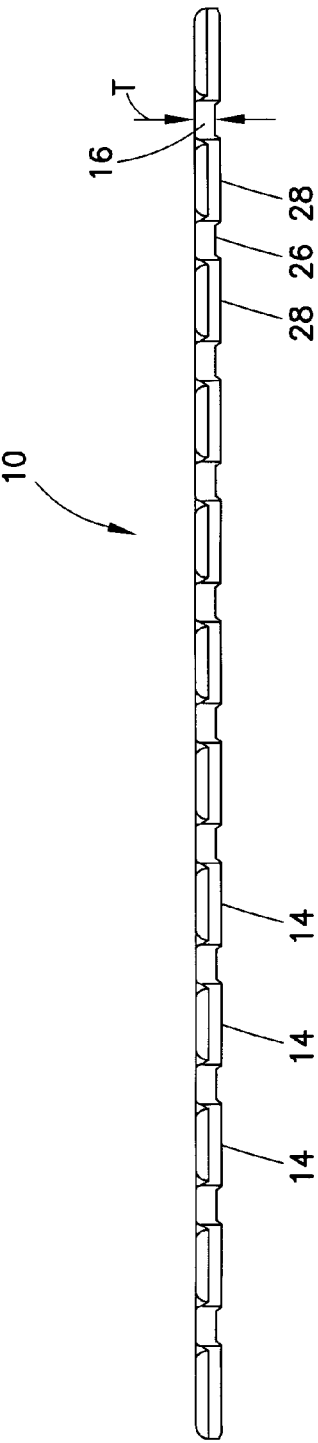
FIG. 2 is a side elevation of the straight plate of FIG. 1.
Figures 3, 4:
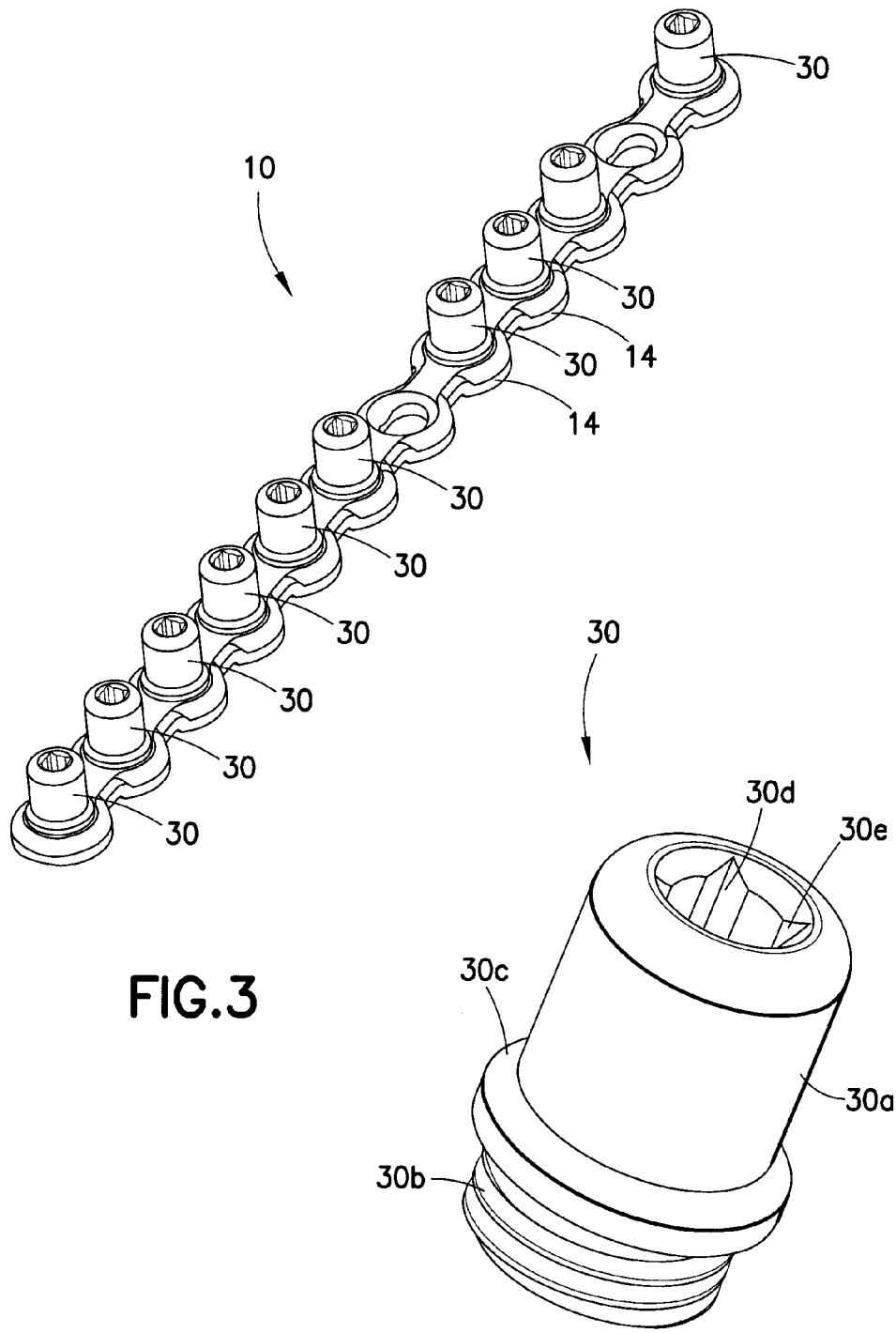
FIG. 3 is an isometric view of the straight plate of FIG. 1, shown with guides preassembled within the locking screw holes of the plate.
FIG. 4 is an isometric view of a guide for use in the system of the invention.
Figure 6:
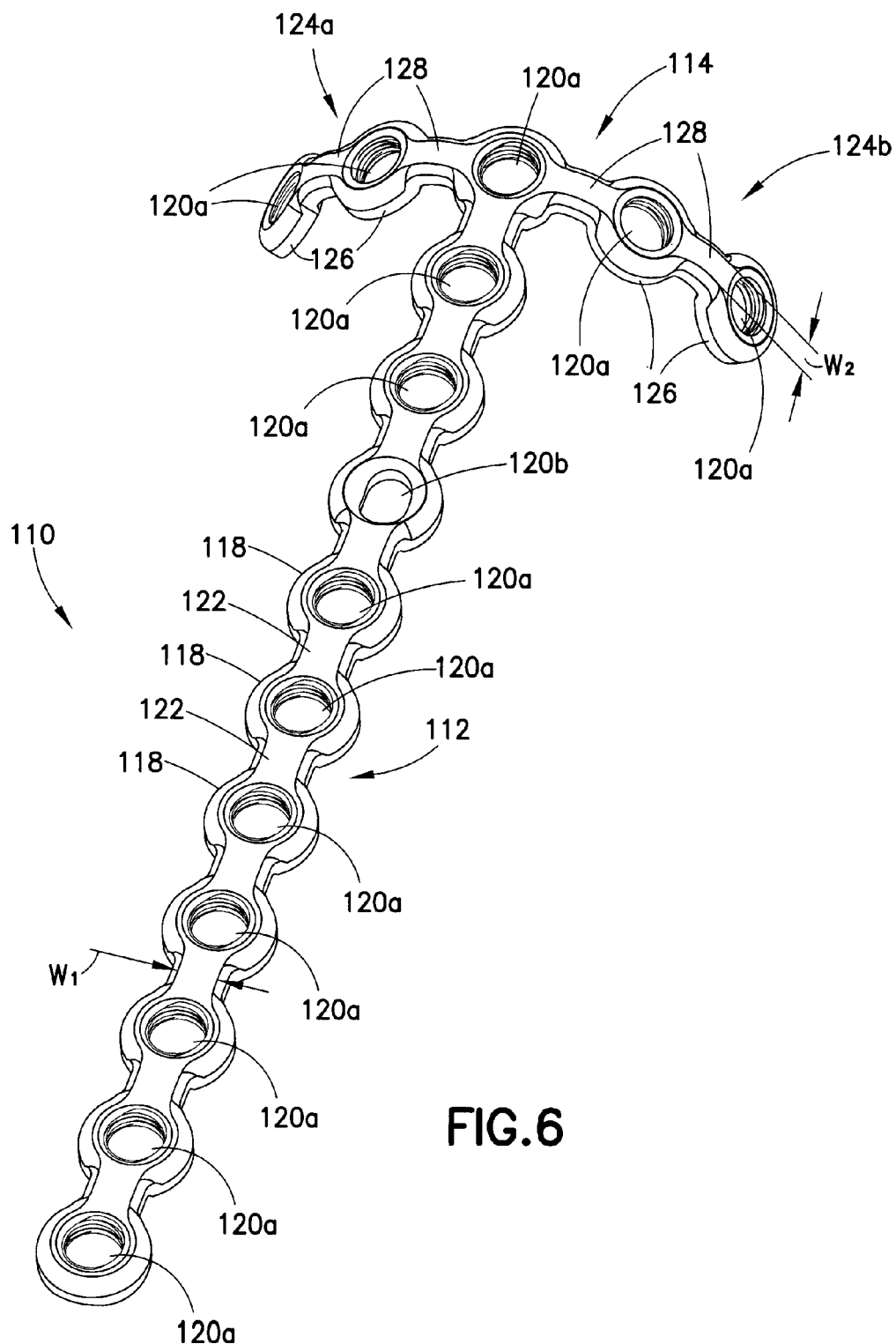
FIG. 6 is an isometric view of the T-shaped plate of FIG. 5.
Figure 10:
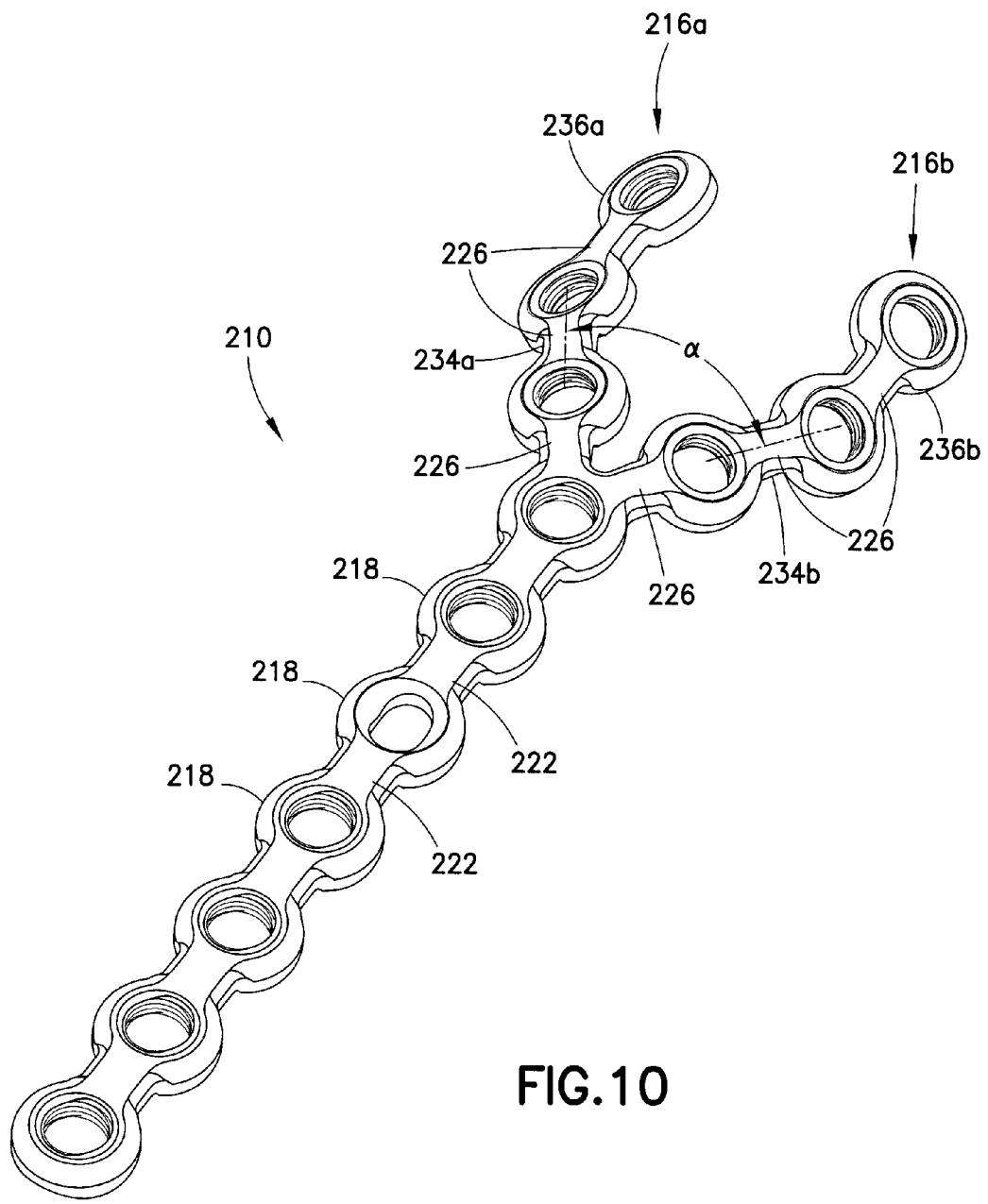
FIG. 10 is an isometric view of the Y-shaped plate of FIG. 9.
Figure 14:
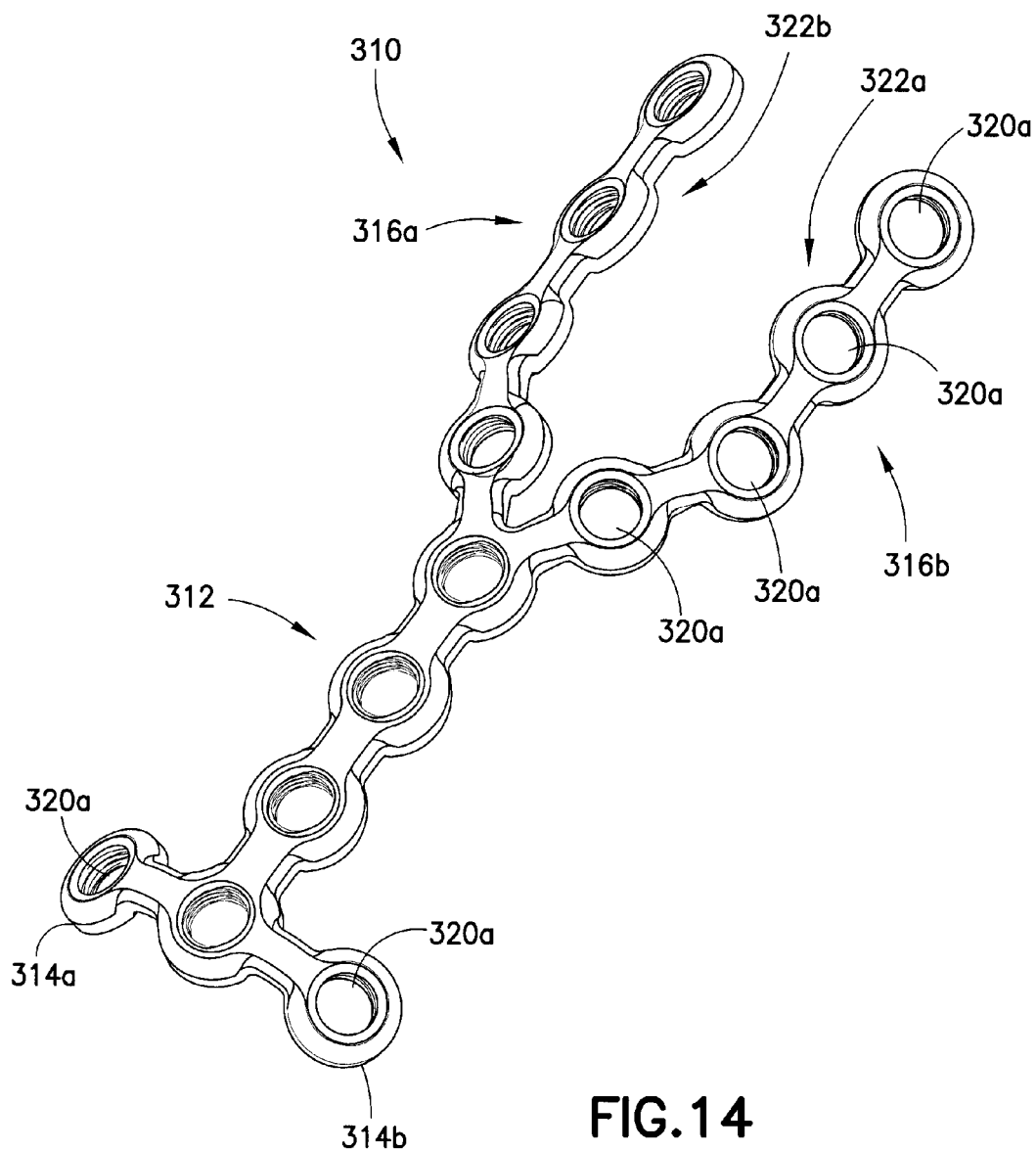
FIG. 14 is an isometric view of the TY-shaped plate of FIG. 13.
Figure 20:
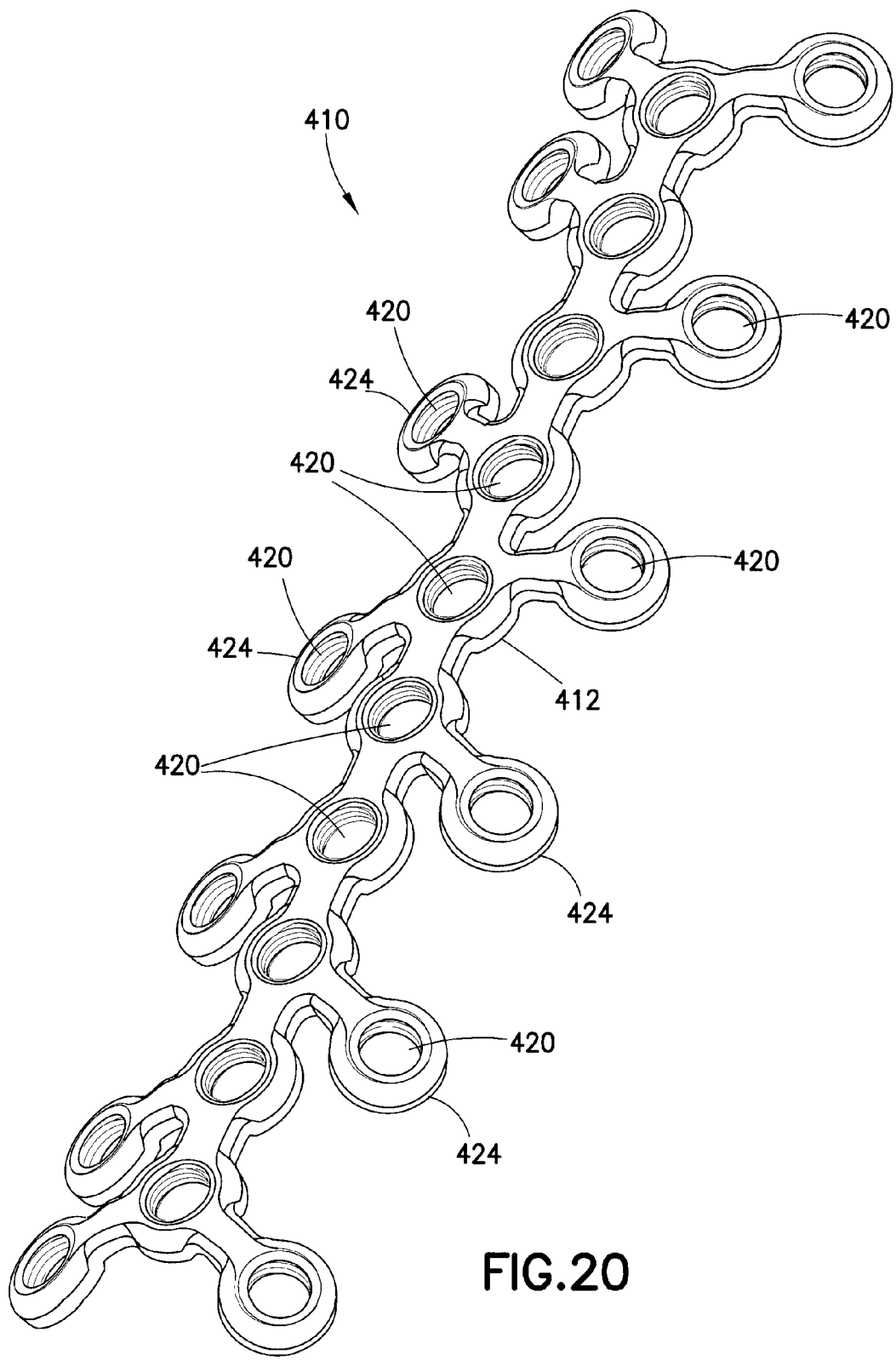
FIG. 20 is an isometric view of the web plate of FIG. 18.

Referring to FIGS. 1 through 3, bone plate 10 is a plate with a straight rail 12 defining a longitudinal axis A of the plate. The rail 12 includes a linear arrangement of ring-shaped screw hole boundaries 14, with adjacent boundaries interconnected by respective webs 16. The webs 16 each have a length L of 1.77, a width W of 3.05 mm, and a thickness T is 1.24 mm. The webs 16 have a lower surface 26 which is recessed relative to the lower bone contacting surfaces 28 of adjacent boundaries. Each boundary 14 defines a screw hole 18a, 18b for receiving a screw. The screw holes are either locking screw holes 18a or elongated non-locking screw holes 18b. Locking screw holes 18a having internal threads 20 for engaging the threads at the head of a locking screw 620 (FIG. 29) or for receiving a guide 30 (FIG. 4), as discussed in more detailed below. The center-center distance C for adjacent locking screw holes is 7.42 mm. Screw holes 18b are dynamic compression plate (DCP) holes each with a respective upper recess 22 for receiving the convex lower surface of a non-locking multidirectional screw 640 (FIG. 31), as also discussed below. The locking and DCP screw holes 18a, 18b may be symmetrically or asymmetrically arranged along the length of the rail. An embodiment of the plate 10 has a length of 90 mm which is ideal for placement on the metacarpal bones.

Referring generally to FIGS. 1, 3 and 4, the threaded locking screw holes 18a are each preferably preassembled with a guide 30. The guide 30 has a cylindrical upper body 30a, a threaded lower portion 30b for engaging locking screw holes 18a, a circumferential lip 30c between the upper and lower portions 30a, 30b that seats on the upper plate surface of a screw hole boundary 14, a bore 30d and a driver engagement structure 30e, e.g., inner corners. As described in co-owned US Pub. Nos. 20060149250A1, 20060161158A1, 20070233111A1, which are hereby incorporated by reference herein in their entireties, and discussed further herein below, the guides 30 and associated tools 500 (also discussed below with respect to FIGS. 23 through 27) facilitate (i) bending the plate while the plate is positioned on the bone, (ii) directing a drill through the threaded holes along the fixed axis of the helical thread without necessitating assembly of a separate drill guide during the surgical procedure, and (iii) repeated stressing of the plate along the web between adjacent guides to cause controlled removal of a portion of the plate. In view of point (iii), plate 10 and all plates of the system, can be readily shortened in length or otherwise modified in shape to accommodate a particular bone fracture, bone feature, or individual patient anatomy.

Referring to FIGS. 5 through 8, bone plate 110 is generally T-shaped, comprising a straight rail 112, substantially similar to rail 12, and a transverse portion 114 at one end of the rail. The rail 112 includes a linear arrangement of ring-shaped screw hole boundaries 118 defining screw holes, described below, with adjacent boundaries connected by respective webs 122. The webs 122 of the rail 112 each have a length $L_1$ of 1.77 mm, a width $W_1$ of 3.05 mm, and a thickness $T_1$ of 1.24 mm. The transverse portion 114 includes two oppositely-directed extensions 124a, 124b at one end of the rail. The extensions 124a, 124b also include screw hole boundaries 126, with adjacent boundaries connected by respective webs 128. Webs 128 each have a length $L_2$ of 1.48 mm, a width $W_2$ of 2.16 mm, and a thickness $T_2$ of 1.4 mm. The larger dimensions of the webs 122 of the rail 112 relative to the webs 128 of the extensions 124a, 124b provide a rail with increased torsional stiffness relative to the extensions. This allows the extensions 124a, 124b to be relatively easily shaped to the bone (as described below) without inadvertently imparting a twist to the straight rail 112. As a result, the surgeon can more freely manipulate the extensions in bending without concern for deformation of the rail. The lower bone contacting surfaces 132 of the boundaries along the extensions 124a, 124b are preferably arranged along a 120°±20° curve (transverse to the longitudinal axis A) at a radius of 13.3 mm to conform to the shape of the bone on which the plate is seated.

An embodiment of the T-shaped plate 110 has an overall length of 73.8 mm, a transverse dimension Dt from the side of one extension to the side of the other extension of 27.6 mm, and a vertical dimension Dv defined between the rail at the center of the extensions and the ends of the extensions of 10.5 mm. In the embodiment shown, the rail 112 includes ten threaded locking screw holes 120a, and one non-locking oblong (DCP) screw hole 120b for dynamic compression of a fracture during fastener insertion through the hole. The DCP screw hole 120b is positioned with seven locking screw holes 120a on side and three locking screw holes 120a on the other side thereof. The extensions 124a, 124b each include two locking screw holes 120a. The T-shaped plate 110 is sized and shaped for metacarpal fractures. As shown in FIG. 8, the threaded locking screw holes 120a of the plate are preferably pre-assembled with guides 30.

Turning now to FIGS. 9 through 12, bone plate 210 is a Y-shaped plated, having a straight rail 212, and two extensions 216a, 216b branched off one end of the rail. The rail 212 is substantially similar to rail 112, with webs 222 having the same web dimensions as 122, but rail 212 may be of different length and may include a different number of screw hole boundaries 218, and have a different number of threaded screw holes and DCP holes. The extensions 216a, 216b have webs 226 with the same dimensional properties as the extensions of the T-shaped plate. The extensions 216a, 216b include respective first portions 234a, 234b angled relative to each other, and second portions 236a, 236b parallel to each other. The first portions 234a, 234b are preferably angled relative to each other in the plane of the rail 212 at an angle α, wherein α=60°±10°. The relatively angled first portions 234a, 234b provide relief to a tendon attachment point. The parallel second portions 236a, 236b extend alongside the bone to saddle or buttress the condyles of either the head or base of the long bones of the hand or foot, e.g., metacarpals, phalanges and metatarsals. The parallel second portions 236a, 236b also permit placement of screw hole boundaries laterally on either side of tendon attachments located on the dorsal side of the head or base of the long bones of the hand or foot. The lower bone contacting surfaces 238a, 238b of the boundaries of the extensions 216a, 216b are preferably arranged along a 60°±5° curve (transverse to the longitudinal axis A) at a radius of 15.2 mm. In one embodiment, the plate 210 has an overall length of 71.9 mm, a transverse dimension Dt from the side of one extension to the side of the other extension of 19.5 mm, and a vertical dimension Dv defined between the rail at the center of the extensions and the ends of the extensions of 4.5 mm. In the embodiment shown, the extensions 216a, 216b each include three screw hole boundaries 218, with the first portions 234a, 234b defined from respective first and second screw hole boundaries, and the second portions 236a, 236b defined from respective second to third screw hole boundaries to engage the condyles of the bone. As shown in FIG. 12, the threaded holes of the plate are preferably pre-assembled with guides 30.

Referring now to FIGS. 13 through 17, bone plate 310 has a straight rail 312, a transverse portion defined by two opposing extensions 314a, 314b at one end forming a T-shape, and two extensions 316a, 316b in a Y-shape configuration at its opposite end; plate 310 is referred to as a TY-shaped plate.

In the embodiment shown, the T-shape portion is generally similar to T-shape plate 110, but is distinguished by each extension 314a, 314b having a single screw hole boundary, each with a locking screw hole 320a on each side of the rail 312. The transverse dimension Dt1 from the side of one extension 314a to the side of the other extension 314b is 19.5 mm, and the overall vertical dimension Dv1 defined between the rail 312 at the center of the extensions and the ends of the extensions of 4.7 mm. The lower bone contacting surfaces 338 of the boundaries of the extensions 314a, 314b are preferably arranged along a 60°±5° curve (transverse to the longitudinal axis A) at a radius of 13.9 mm.

The Y-shaped portion is generally similar to Y-shaped plate 210, but is distinguished by each extension 316, 316b having four screw hole boundaries, each with a threaded screw hole 320a, with three screw holes in each of the parallel second portions 322a, 322b. The transverse dimension Dt2 from the side of one extension 322a to the side of the other extension 322b is 19.5 mm, and the overall vertical dimension Dv2 between the rail 312 at the center of the extensions 316a, 316b and the ends of the extensions is 4.5 mm. The lower bone contacting surfaces 340 of the boundaries of the extensions are also preferably arranged along a 60°±5° curve (transverse to the longitudinal axis A) at a radius of 15.2 mm.

The webs 322 of the rail 312 each have a length of 1.77 mm, a width of 3.05 mm, and a thickness of 1.24 mm. The webs of the extensions each have a length of 1.48 mm, a width $W_2$ of 2.16 mm, and a thickness of 1.4 mm. Thus, the webs of the rail are stiffer than the webs of the extensions. The plate 310 has an overall length of 55.5 mm. The TY-shaped plate is preferably sized and shaped to conform to the bone for metacarpal fractures. As shown in FIG. 17, the locking screw holes in the plate are preferably pre-assembled with guides 30.

Turning now to FIGS. 18 through 22, bone plate 410 includes a straight rail 412 with screw hole boundaries 418, and a plurality of extensions 424 extending from the screw hole boundaries at each side of the rail. The extensions 424 each include a single screw hole boundary 418. The webs 422 of the rail 412 each have a length $L_1$ of 1.77 mm, a width $W_1$ of 3.05 mm, and a thickness of 1.24 mm. Webs 428 of each extension have a length $L_2$ of 1.48 mm, a width $W_2$ of 2.16 mm, and a thickness of 1.4 mm. In one embodiment of the plate 410, the terminal boundaries of the rail are each provided with two extensions in (opposing) Y-shaped configurations 432a, 432b, and a relatively longitudinally central boundary is provided with two extensions 424a, 424b in a diagonally opposed relationship. The remaining boundaries include only a single web at an oblique angle relative to the longitudinal axis A. In the embodiment shown in FIGS. 18 through 21, along a first side of the plate four adjacent extensions 424 are in a parallel relationship, non-orthogonally angled relative to the longitudinal axis A in the plane of the rail at an angle β, wherein β=60°, and three adjacent extensions are in a parallel relationship, at an opposite angle –β relative to the longitudinal axis A. Along a second side of the plate, three adjacent extensions are in a parallel relationship, non-orthogonally angled at β in the plane of the rail relative to the longitudinal axis A, and three adjacent extensions are in a parallel relationship at an opposite angle –β relative to the longitudinal axis A.

Figures 21, 22:
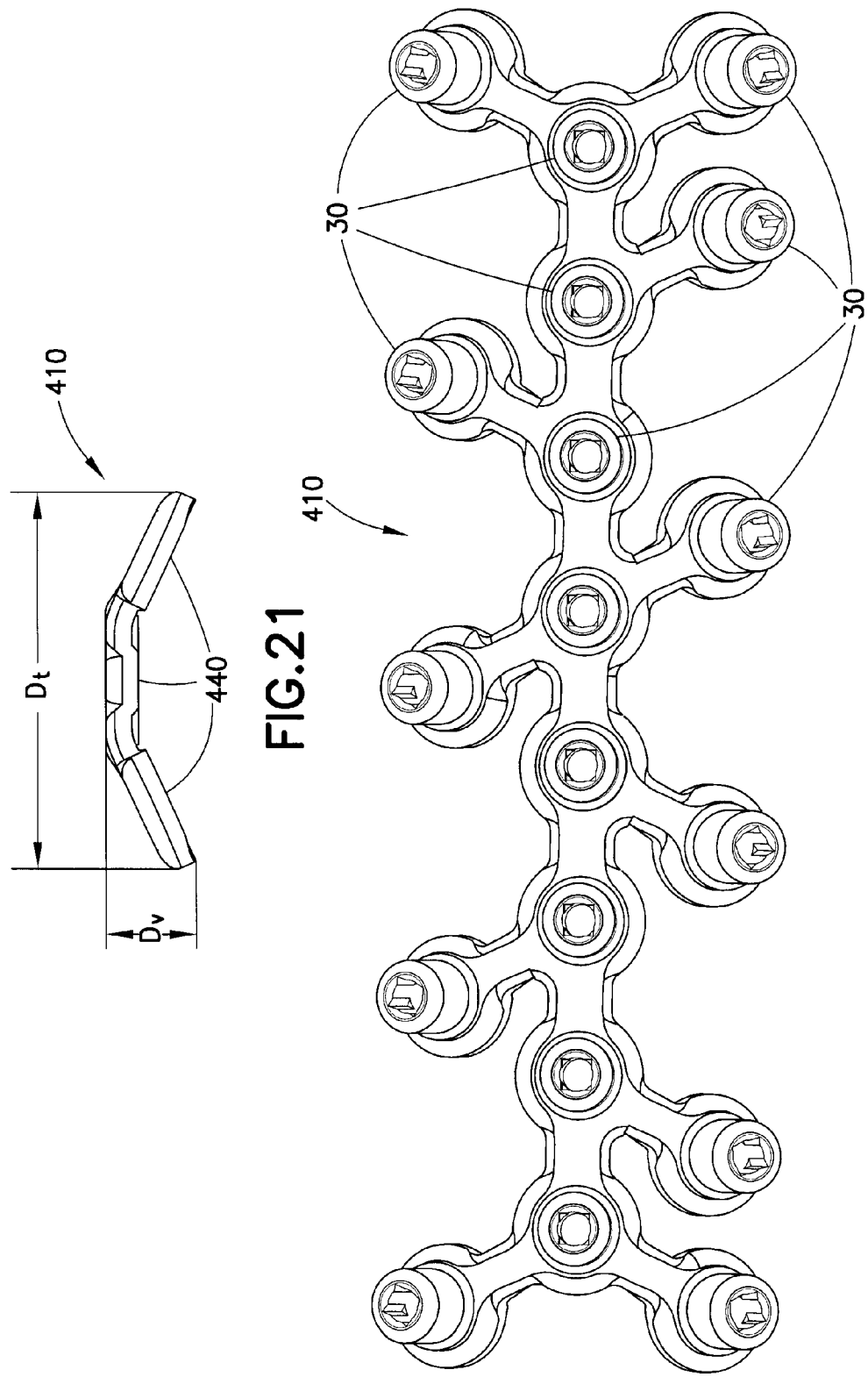
FIG. 21 is an end view of the web plate of FIG. 18.
FIG. 22 is a plan view of an alternate web plate, shown with guides pre-assembled within the locking screw holes of the plate.

Referring to FIG. 21, the transverse dimension Dt from the side of an extension on one side of the rail to an extension on the other side of the rail is 17.4 mm, and the overall vertical dimension Dv between the rail at the center of the extensions and the ends of the extensions of 4.5 mm. The lower bone contacting surfaces 440 of the boundaries of the extensions are also preferably arranged along a 60°±5° curve (transverse to the longitudinal axis A) at a radius of 11 mm. As seen best in FIGS. 19 and 20, the arrangement of the extensions 424 relative to the rail 412 provides a staggered arrangement of threaded screw holes 420 such that the fixed angle trajectory of the axes of the holes in the extensions 424 do not intersect the trajectories of the axes of the threaded screw holes in the rail 412. The plate 410, referred to as a web plate is both laterally and longitudinally asymmetrical, with higher plate hole density at the ends of the plate and along one side of the plate. The asymmetrical shape of the web plate allows a surgeon to select to which side of the straight rail (left or right) a larger concentration of screw hole boundaries will be provided on the bone by rotating the plate about an axis normal to the top surface of the plate. (FIG. 22 shows a similar plate oriented to provide a higher concentration of plate holes along an opposite side relative to the plate in FIG. 19). The web plate 410 also provides a net or cage along the bone shaft for high energy or segmental bone loss application. This can be accomplished by bringing the extensions in along the bone and leaving them unfilled with bone graft. The web plate 410 is preferably sized and shaped to conform to the bone for metacarpal fractures, and is designed to maintain the length of a bone even where there is extensive bone loss due to injury. The plate of FIGS. 18 through 21 has a length of 79 mm. As shown in FIG. 22, the plate may have a shorter rail with fewer screw hole boundaries and thus a shorter length. Similarly, the plate may have a longer rail with more screw hole boundaries and thus a longer length. As also seen in FIG. 22, the locking screw holes in the web plate 410 are preferably pre-assembled with guides 30.

Figures 23, 24:
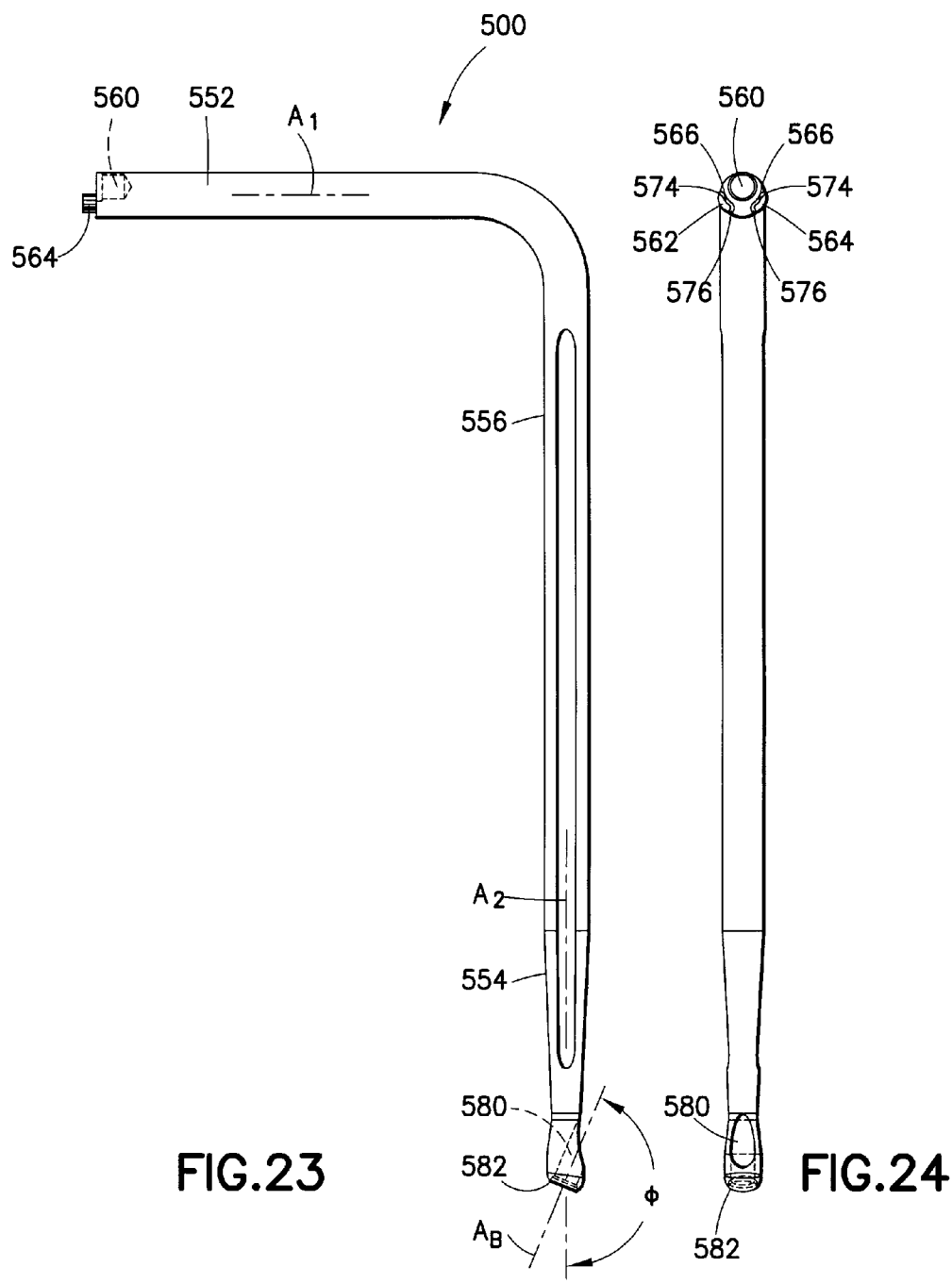
FIG. 23 is a side elevation of a bending tool for manipulating a plate via the guides preassembled to the plate.
FIG. 24 is a side elevation of the tool of FIG. 23, shown rotated 90° relative thereto.

As discussed above, each of the plates is preferably pre-assembled with guides 30. Referring to FIGS. 23 and 24, plate bending tools 500 (one such tool is shown, however the tools are generally used in pairs) may be attached to the guides and/or plate while the plate is located on or off the bone to effect alteration of the plate shape in an effective and precise manner. Each bending tool 500 includes an L-shaped shaft 556 extending between a first end 552 and a second end 554, with the first and second ends 552, 554 integrally formed at the respective ends of the shaft 556, and at least a portion of the shaft 556 defining a handle for gripping and manipulation by a user. The first end 552 defines a longitudinal axis $A_1$, the second end defines a longitudinal axis $A_2$, and axes $A_1$ and $A_2$ are orthogonal relative to each other. The only distinction between the two tools of a pair of tools is that the handles 556 of a pair extend in opposite directions relative to each other.

Figure 25:
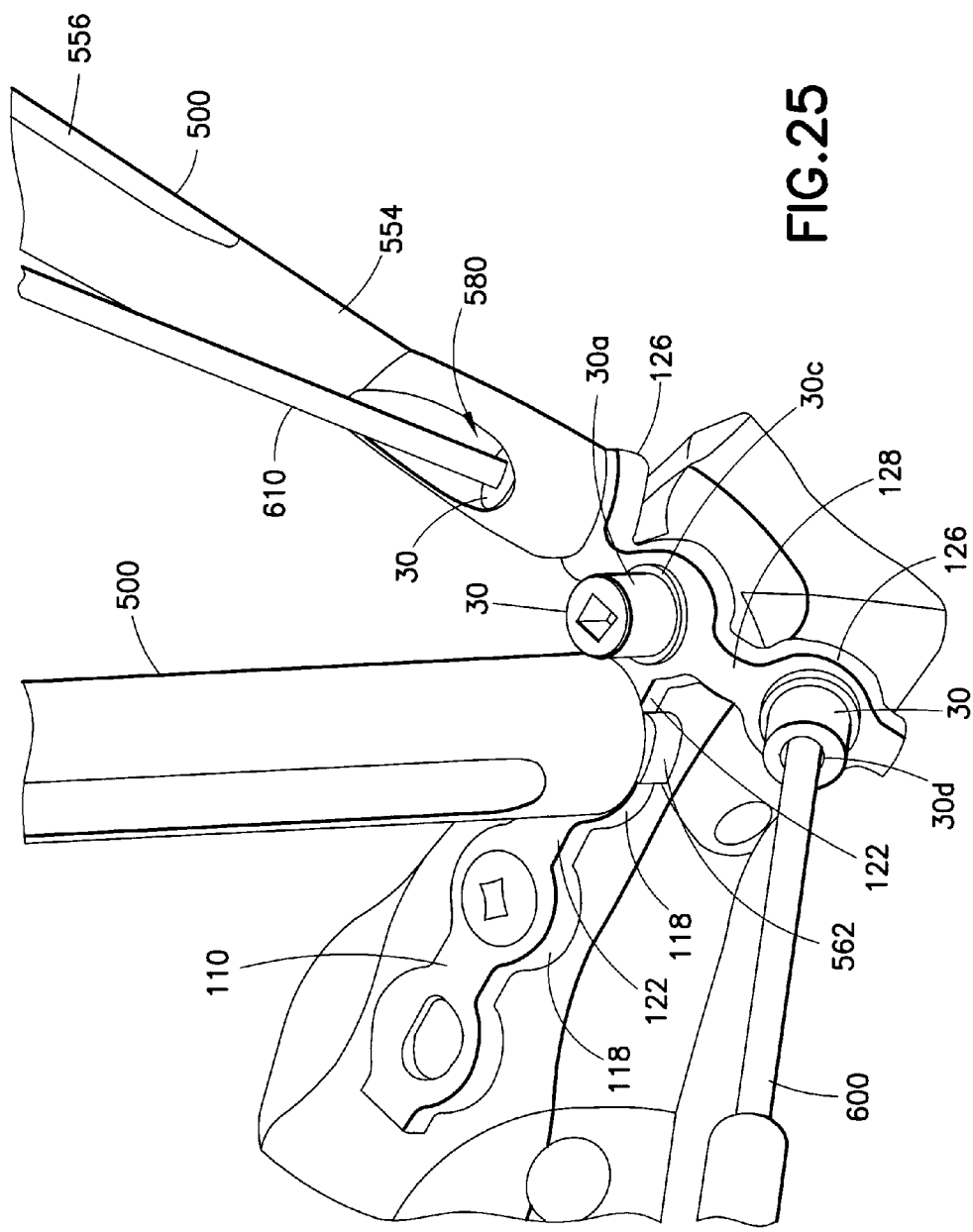
FIG. 25 illustrates a method of assembling a T-shaped plate to bone with the tools of FIG. 23.

Referring to FIGS. 23, 24 and 25, the first end 552 defines a socket 560 sized to closely receive the tip 30a of a guide 30, and means for rotationally fixing the first end 552 relative to a portion of the bone plate, such as the webs 122, 128 of T-shaped plate 110, although the tools work the same with any of the plates. In a preferred embodiment, the means for rotationally fixing the first end relative to the bone plate are two feet 562, 564 that straddle the webs 122, 128 of the plate 110. The two feet 562, 564 include curved inner surfaces 566 that seat about the radiused screw hole boundaries 118, 126 of the plate to quickly and easily align the tool 500 on a plate. The feet 562, 564 each have a toe end 574 for abutting the web, e.g., 122, at a fulcrum location, and a heel end 576 for applying force to a screw hole boundary 118. Then, rotation of the second end 554 of the handle 556 relative to the plate 110 imparts a force to the plate that effects bending of the plate in the plane of the plate about the fulcrum. The second end 554 of the tool defines a bore 580 with a central longitudinal axis $A_B$ oriented an oblique angle relative to the longitudinal axis $A_2$ of the second end 554. The angle φ between $A_2$ and $A_B$ is 160°±15°. The bore 580 is sized in diameter to be closely received over the tip 30a of the guide 30. The bore 580 preferably includes an enlarged lower portion 582 for receiving the shoulder portion 30c of the guide 30 so that the tool can seat flush on the upper surface of the plate. The bore 30d of the guide 30 is also sized to receive a drill guide 600 (for drilling a screw hole through the guide) and a K-wire 610 (for temporary fixation of the plate through the guide).

Figure 26:
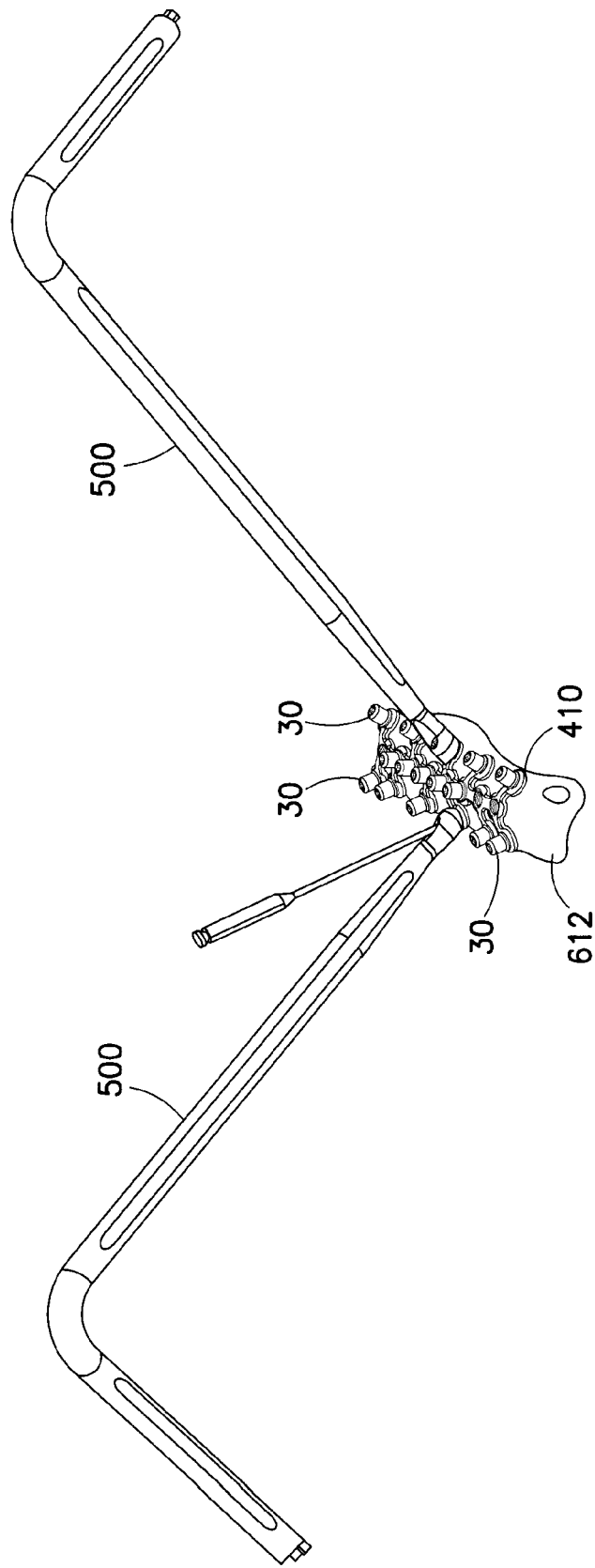
FIG. 26. illustrates a method a assembling a web plate to bone with the tools of FIG. 23.
Figure 27:
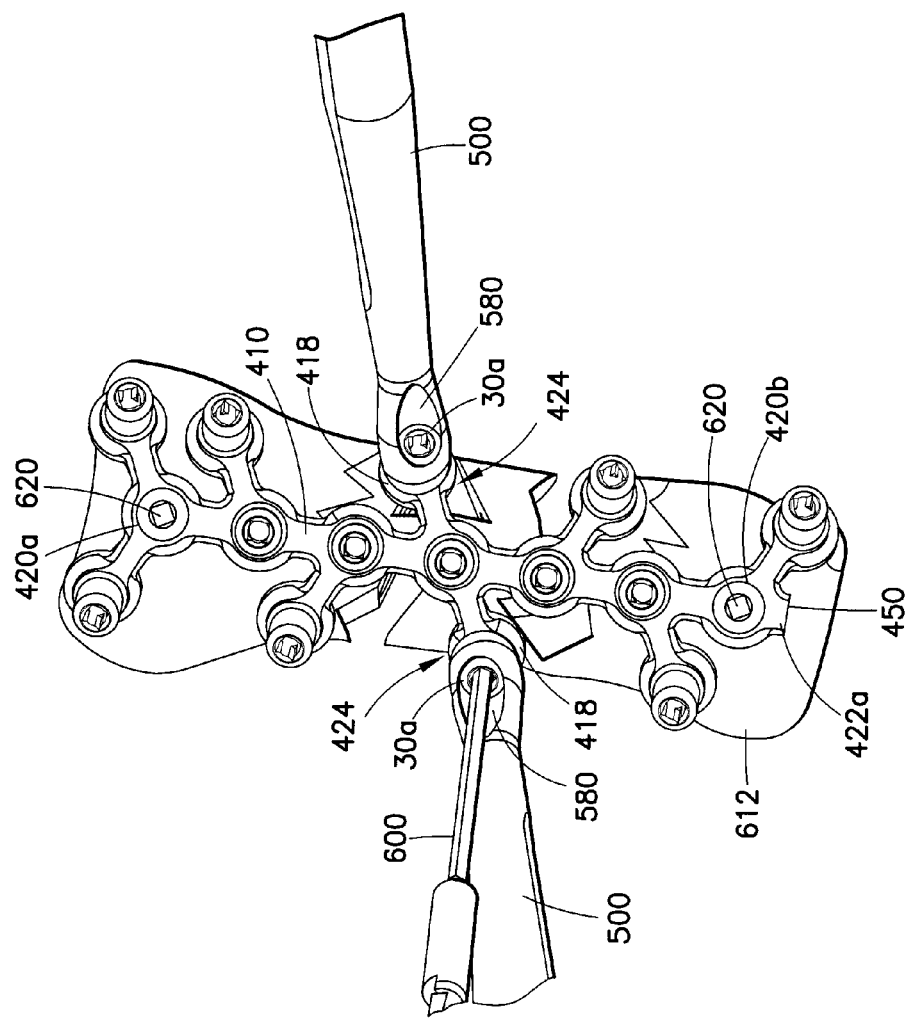
FIG. 27 is a top view of the method of FIG. 26.

Referring to FIGS. 26 and 27, a web plate 410 is shown with guides 30 preassembled thereto. The web plate 410 has been shortened from an initial length through the use of the tools. That is, tools 500 have been coupled to guides 30 on either side of the web 422a which is to be a new terminus of the plate, and the tools are operated to repeatedly reverse bend the plate at the web 422a in the longitudinal direction until the plate separates at the web to reduce the length of the plate and provide a new plate terminus 450. Such ability to remove and method of removing a portion of a plate applies to all plates of the system and all portions of the plates, including any extension thereof, or portions of extensions thereof.

The plate 410 is provisionally coupled to a small long bone such as a phalangeal bone 612 (or metacarpal bone) with screws 620 inserted through an end locking screw hole 420a and the locking screw hole 420b of the new terminus 450 thereof and into the bone 612.

Figure 28:
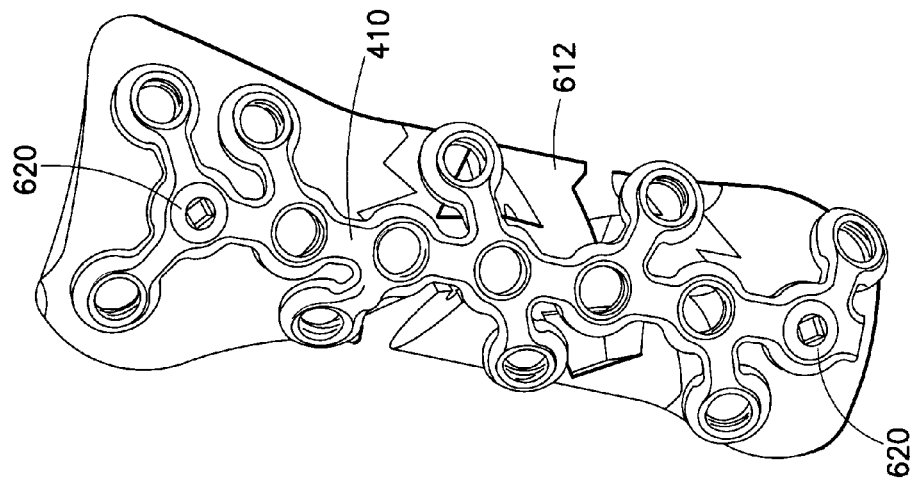
FIG. 28 illustrates the web plate shaped to the bone.

The extensions 424 of the plate 410 are shaped to the bone 612 with the tools 500. The bores 580 of respective tools 500 are positioned over the bodies 30a of the guides 30 and appropriate relative force is applied to re-orient the screw hole boundaries 418 as necessary to (i) seat the bone contacting surface of the plate close to the underlying bone and/or (ii) orient the locking screw hole axes such that locking screws inserted through the locking screw holes will be oriented in a desired direction so as to engage desired bone and bone fragments without interference with other locking screws. With the bending tools 500 coupled to the guides and plate in the described manner, the plate 410 may be bent along any web in concave and convex directions (longitudinally) and rotationally along an axis of any web (in torsion). The screw hole boundary of each extension can be oriented independently of all other screw hole boundaries. Once a web has been bent to orient a screw hole boundary 418, a K-wire may be inserted through the bores of the tool 500 and guide 40 to temporarily fix the location of the boundary (and overcome any springback in the plate)(as shown in FIG. 25), or a hole may be drilled through the bores of the tool 500 and guide 30 with drill 600 for receiving a locking screw. The bore 580 of the tool 500 is sized so that the tool may be withdrawn from over the K-wire, guide and/or drill, while leaving such components in place relative to the plate. Once the hole is drilled, the guide 30 may be removed and a locking screw 620 may be inserted. FIG. 28 illustrates the plate 410 fully shaped over the bone 612 and fragments, with guides removed. It should be appreciated that additional locking screws 620 may be inserted through the plate 410 and into the bone throughout the plate shaping procedure.

While the above plates have dimensions particularly suitable for metacarpal application, the shapes, structures, and benefits or such plate are equally applicable to treatment of fractures of smaller long bones such as the phalanges. However, it is anticipated that the plates will be scaled down in size (with appropriately scaled dimensions for plate holes, rail webs, extension webs, lengths, etc.) for use on such smaller bones. An appropriate scaling for phalangeal application would be plates seventy percent of the size of the plates described above for metacarpal use.

Figures 29, 30:
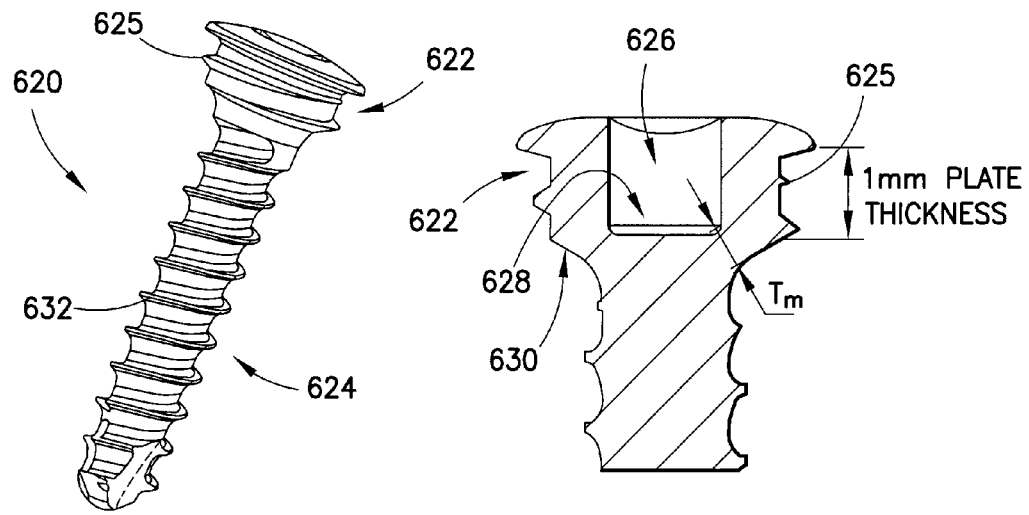
FIG. 29 is a perspective view of a locking screw according to the invention.
FIG. 30 is a broken section view of the locking screw of FIG. 29.

Turning now to FIGS. 29 and 30, a locking screw 620 is provided specifically for use with thin scaled-down plates (approximately 1 mm thick) such as for treating phalangeal fractures. The locking screw 620 is preferably made from cobalt chrome alloy. The locking screw 620 includes a head 622 and shaft 624. The head has machine threads 625 that extend about 1.0±0.1 mm of vertical distance of the head. The head 622 also has a non-circular socket 626 with a flat bottom recess 628 that optimizes the material thickness $T_m$ between the socket 626 and a lower surface 630 of the head. The minimum material thickness $T_m$ is preferably 0.4±0.1 mm, and allows a socket 626 with sufficient driver engagement without reducing the torsional strength of the head to shaft attachment relative to screws for designed for larger plates. The above features provide a screw with a low profile head design but the strength of a larger screw. The shaft 624 preferably has bone engaging threads 632, but may optionally be smooth. The thin low profile of both the plate and the locking screw minimizes soft tissue irritation.

Figure 31:
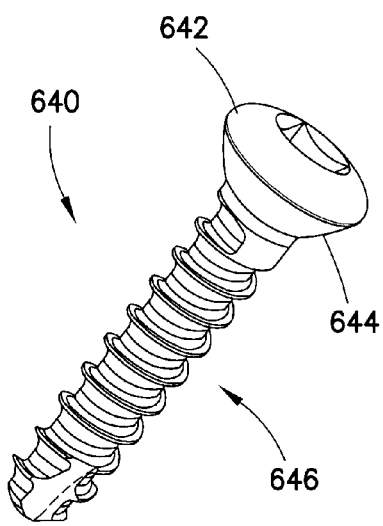
FIG. 31 is a perspective view of a non-locking screw according to the invention.

Referring to FIG. 31, a non-locking multidirectional screw 640 is also provided for use in the non-locking holes of the plates of the system. The screw 640 is preferably made of titanium alloy. Screw 640 has a non-threaded head 642, preferably with a rounded lower surface 644, and a threaded shaft 646. Each of the locking and non-locking screws 620, 640 may be provided in various lengths. In addition, all the holes of the various plates may be locking, non-locking, or in a different locking/non-locking arrangement than described above to receive the screws 620, 640.

The plates of the system are uniquely shaped for fixation of most types of metacarpal/phalanx fractures. The straight plate 10, T-shaped plate 110, Y-shaped plate 210, TY-shaped plate 310, and web plate 410 provide all the shapes required for fixation of all fractures in such small bones, and as a kit or system provide options for small long bone fixation that is not available in any other kit or system. Such shapes are each highly configurable through the shaping procedure described herein so as to adaptable to individual patients and the unique circumstances of a given fracture. Further, by changing the length of the various plates (through reverse bending), the functional structural aspects of the individual plates remains. In addition, given the high symmetry in certain individual plates (each of the straight plate, T-shaped plate, Y-shaped plate, and TY-shaped plate are laterally symmetrical), they are adapted for both left and right hand use. Moreover, the asymmetry of the web plate permits the surgeon to concentrate fasteners to one side of bone, if required. Each of the plates of the present system may be formed from any one of numerous materials known in the art, including stainless steel, titanium, and titanium alloy such as Ti-6Al-4V.

There have been described and illustrated herein embodiments of a system for treating small bone fractures, including bones of the metacarpals and phalanges, and individual plates therefor. In addition, methods of customizing the plates to various bones are described. While particular embodiments of the invention have been described, it is not intended that the invention be limited thereto, as it is intended that the invention be as broad in scope as the art will allow and that the specification be read likewise. By way of example, various dimensions of the plates sized for metacarpal application are provided, as well as a scaling factor for plates for smaller bones. While preferred dimensions for plates for such application are provided, it is appreciated that variations in dimension (e.g., ±ten percent) are permissible provided such variations do not cause the extensions to have a higher torsional stiffness than the rail in the respective plates. It will therefore be appreciated by those skilled in the art that yet other modifications could be made to the provided invention without deviating from its spirit and scope as claimed.

What is claimed is:

1. A method of implanting a bone plate on a bone, comprising:
   a) providing a bone plate having a plurality of tubular drill guides pre-assembled to threaded locking holes of the bone plate;
   b) providing first and second tools, each tool having,
      i) a shaft extending between first and second ends of the shaft, wherein the first end has a first longitudinal axis and the second end is straight and defines a second longitudinal axis transverse to the first longitudinal axis, at least a portion of the shaft functioning as a handle for the tool,
      ii) the first end defining a socket parallel with the first longitudinal axis and including structure for straddling a portion of the bone plate to rotationally fix the first end relative to the bone plate, and
      iii) the second end defining a bore within the shaft, the bore having a bore axis obliquely oriented relative to the second longitudinal axis,
   c) positioning the bore of the second end of the first tool over a first tubular drill guide on the bone plate, and coupling either the first end or second end of the second tool to a second tubular drill guide; and
   d) manipulating the tools relative to each other to bend portions of the plate relative to each other.

2. A method according to 1, further comprising:
   while maintaining the position of the first tool on the first tubular drill guide, inserting a drill through the first tubular drill guide to drill a hole into the bone.

3. A method according to 1, further comprising:
   while maintaining the position of the first tool on the first tubular drill guide, inserting a k-wire through the first tubular drill guide and the bore of the second end of the shaft to fixate the plate to the bone.

4. A method according to claim 3, further comprising:
   after inserting the K-wire, withdrawing the first tool from over the K-wire.

5. A method according to claim 1, wherein:
   said manipulating includes reverse bending to cause stressing of the plate and consequent removal of a portion of the plate.

6. A method according to claim 1, wherein:
   the second end of the tool includes an end face about the bore, and said positioning the bore of the second end of the first tool over a first tubular drill guide on the bone plate further includes positioning the end face against the bone plate.

7. A method according to claim 6, wherein:
   the end face is oriented at an oblique angle relative to the second longitudinal axis, and the bore axis and the second longitudinal axis extend through the end face.

8. A method according to claim 7, wherein:
   wherein the bore axis and the second longitudinal axis intersect at the end face.

9. A method of implanting a bone plate on a bone, comprising:
   a) providing a bone plate having a plurality of tubular drill guides pre-assembled to threaded locking holes of the bone plate;
   b) providing a first tool having a shaft extending between first and second ends of the shaft, wherein the first end has a first longitudinal axis and the second end is straight and defines a second longitudinal axis transverse to the first longitudinal axis, and the second end defining a bore within the shaft, the bore having a bore axis obliquely oriented relative to the second longitudinal axis;
   c) providing a second tool having a shaft extending between first and second ends of the shaft, the first end having a first longitudinal axis, and the first end defining a socket parallel with the first longitudinal axis and including structure for straddling a portion of the bone plate to rotationally fix the first end relative to the bone plate, at least a portion of the shaft functioning as a handle for the second tool;
   d) positioning the bore of the second end of the first tool over a first tubular drill guide on the bone plate;
   e) positioning the socket of the first end of the second tool over a second tubular drill guide and the structure for straddling a portion of the bone plate about a portion of the bone plate; and
   f) manipulating the first and second tools relative to each other to bend portions of the plate relative to each other.

10. A method according to claim 9, wherein:
    at least a portion of the shaft of the first tool functions as a handle for the first tool, and at least a portion of the shaft of the second tool functions as a handle for the second tool.

11. A method according to 9, further comprising:
    while maintaining the position of the first tool on the first tubular drill guide, inserting a drill through the first tubular drill guide to drill a hole into the bone.

12. A method according to 9, further comprising:
while maintaining the position of the first tool on the first tubular drill guide, inserting a k-wire through the first tubular drill guide and the bore of the second end of the shaft to fixate the plate to the bone.

13. A method according to claim 12, further comprising:
after inserting the K-wire, withdrawing the first tool from over the K-wire.

14. A method according to claim 9, wherein:
said manipulating includes reverse bending to cause stressing of the plate and consequent removal of a portion of the plate.

15. A method according to claim 9, wherein:
the second end of the first tool includes an end face about the bore, and said positioning the bore of the second end of the first tool over the first tubular drill guide on the bone plate further includes positioning the end face against the bone plate.

16. A method according to claim 15, wherein:
the end face is oriented at an oblique angle relative to the second longitudinal axis, and the bore axis and the second longitudinal axis extend through the end face.

17. A method according to claim 16, wherein:
wherein the bore axis and the second longitudinal axis intersect at the end face.

* * * * *